United States Patent [19]

Collen

[11] 4,216,291

[45] Aug. 5, 1980

[54] THROMBOSIS-TEST

[75] Inventor: Desire J. Collen, Winksele, Belgium

[73] Assignee: Leuven Research & Development V.Z.W., Louvain, Belgium

[21] Appl. No.: 949,631

[22] Filed: Oct. 10, 1978

Related U.S. Application Data

[63] Continuation of Ser. No. 723,187, Sep. 13, 1976, abandoned.

[30] Foreign Application Priority Data

Sep. 19, 1975 [NL] Netherlands ......................... 7511055

[51] Int. Cl.$^2$ ......................... C07G 7/00; C07G 7/02; G01N 31/14; G01N 33/16
[52] U.S. Cl. ..................................... 435/7; 23/230 B; 260/112 R; 424/12; 435/13
[58] Field of Search ................. 195/103.5 A, 103.5 R, 195/99; 424/12, 85, 88; 23/230 B; 435/7, 13; 260/112 R

[56] References Cited

U.S. PATENT DOCUMENTS 3,912,805 10/1975 Cayzer et al. ................. 195/103.5 X

OTHER PUBLICATIONS

Collen et al., A Tanned Red Cell Hemagglutination Inhibition Immunoassay (TRCHII) for the Quantitative Estimation of Thrombin-Antithrombin III and Plasmin-Alpha-Antiplasmin Complexes in Human Plasma, Thrombosis Research, vol. 7 1975, pp. 235-238.
Collen, D., Emergence in Plasma During Activation of the Coagulation or Fibrinolytic Systems of Neoantigens, Associated with the Complexes of Thrombin or Plasmin with their Inhibitors, Thrombosis Research, vol. 5, 1974, pp. 777-779.
Collen et al., Immunochemical Distinction Between Antiplasmin and Alpha$_1$-Antitrypsin, Thrombosis Research, vol. 7 1975, pp. 245-249.
Merskey et al., A Rapid, Simple, Sensitive Method for Measuring Fibrinolytic Split Products in Human Serum, Proc. Soc. Exp. Biol. Med., vol. 131 1969, pp. 871-875.

*Primary Examiner*—David M. Naff
*Attorney, Agent, or Firm*—Lewis H. Eslinger

[57] ABSTRACT

A thrombosis test is based on the presence of specific, newly-found, enzyme-inhibitor complexes (such as plasmin-antiplasmin, plasmin-$\alpha_2$-macroglobulin, thrombin-antithrombin-III) in blood samples having an activated blood coagulation and/or fibrinolytic system. The test is immunochemical and uses a purified antiserum which has been generated against the enzyme-inhibitor complex. The antiserum is purified by incubating the antiserum with plasminogen and fresh blood plasma and isolating a gamma globulin fraction containing antibodies specific to the enzyme-inhibitor complex. A reagent for the test is prepared by contacting a blood cell suspension or a latex of particles of synthetic resin with the purified antiserum to obtain a suspension or latex in which antibodies from the antiserum are present on the surface of the cells or particles.

8 Claims, No Drawings

THROMBOSIS-TEST

This is a continuation of application Ser. No. 723,187, filed Sept. 13, 1976, now abandoned.

The invention relates to a thermobosis-test to be carried out clinically, as also in the preparation of the reagentia needed therefor.

After operations, confinements, serious injuries or infectious diseases there is often a great chance of thrombosis in the veins, whilst a thrombosis in the arteries often occurs with sufferers of arteriosclerosis. Furthermore, some patients show a reverse deviation which is known as hyperfibrinolysis. In view of the serious consequences these phenomena may have, such as embolism, cerebral haemorrhages, heart-infarcts, it is desirable to dispose of clinical diagnosis-tests with which the possibility of intravenous blood-coagulation may be determined in an early stage already.

Much research has already been done with regard to the mechanism of blood-coagulation. It has been found that in the human blood-plasma there occurs a group of proteins or coagulation factors which play a part in this blood-coagulation. Under the influence of enzymes, each coagulation factor may be modified from an inactive form to an active form whereby this activation reaction may be activated and inhibited by catalysts and inhibitors, respectively. It has also been found that all activation reactions together constitute a continuous chain of reactions, the so-called coagulation cascade in which the product of each reactions occurs as an enzyme in the subsequent reaction. So, the last step but one of the coagulation cascade consists of a modification of prothrombine into thrombine under the influence of an enzyme in addition to calcium ions and phosphilipides, while the thrombin formed thereby, in its turn, acts as an enzyme in the final step in which fibrinogen is modified into fibrin.

Furthermore, it has been found that in bloodplasma there occurs another group of proteins which together form the so-called fibrinolytic system which acts as a complement of the blood-coagulation system. Also here, each factor of this system, under the influence of enzymes, may be modified from an inactive form into an active form, while the activation reactions together form a fibrinolytic cascade in which the product of each reaction acts as an enzyme in the subsequent reaction. The last step, but one in the cascade, is a modification of plasminogen into plasmin which plasmin may then act as an enzyme in the final step, namely a modification of fibrin into fibrin-breakdown-products. Therefore, the effect of the fibrinolytic system is reverse to that of the blood-coagulation system. Practically always, an activation of the blood-coagulation system is coupled with an activation of the fibrinolitic system (secondary fibrinolysis).

In normal sound blood both systems keep in balance with each other and are relatively inactive. However, if one of the two systems is strongly activated in consequence of disease, injury or the like, the equilibrium may be disturbed so that intravenous blood-coagulation or hyperfibrinolysis will occur.

Some clinical tests with which the possibility of intravenous blood-coagulation and/or hyperfibrinolysis may be ascertained, are already being used. These tests are based on the determination of active or inactive components of the blood-coagulation system or fibrinolytic system in the bloodplasma. They are, however, not sufficiently sensitive for detecting a slow and/or regional activation of one of these systems.

Moreover, methods have been proposed in which products emanating from thrombin-or plasmin-breakdown of fibrinogen are determined quantitatively. For a synopsis, reference is made to the publication by Fletcher and Alkjaersig, Laboratory diagnosis of intravascular coagulation, in the book Recent Advances in Thrombosis, Ed. L. Poller, Churchill Livingstone, Edinburgh, 1973, p. 87 ff. These methods, however, are still too aspecific, too complicated or too protracted so that they are not well applicable in the medical clinic.

So, there remains the need of simple, sensitive and clinically applicable tests for laboratory diagnosis of intravascular blood-coagulation and hyperfibrinolysis in bloodplasma. Now it is the object of the invention to fill this need.

Tests preceding the invention have revealed that the enzymes of the blood-coagulation system and fibrinolytic system emanating from activation in a specific step of the cascade are neutralized in the bloodplasma rather rapidly by the available inhibitors whilst forming enzyme-inhibitor-complexes. These enzyme-inhibitor-complexes may be isolated with physical-chemical agents and are then found to be pretty stable so that they may be stored in their isolated state for quite some time.

It has also been found that the newly detected enzyme-inhibitor-complexes have a specific immunogenic structure which deviates from the structure of (inactive) factors known before. This has made it possible to develop antisera and antibodies against the enzyme-inhibitor-complexes in question, which antisera and antibodies may then serve as agents in a direct determination of the particular enzyme-inhibitor-complexes in human bloodplasma in an immunochemical way.

The invention now provides a method of determining the activation of the blood-coagulation- or fibrinolytic system in bloodplasma which is characterized in that the presence of specific enzyme-inhibitor-complexes which form part of the activated blood-coagulation- or fibrinolytic system in the bloodplasma to be examined is determined in an immunochemical way.

Determination of the presence of the complexes in question may be done in various manners so that various ways of realisation are possible. So, the bloodplasma to be examined may be contacted with a supension of red bloodcells or particles of synthetic resin which bear a purified enzyme-inhibitor-complex on the surface, and with an antiserum against the particular enzyme-inhibitor-complex, and then it is ascertained whether or not agglutination occurs (agglutination-inhibiting test).

Presently the determination is carried out by contacting the bloodplasma to be examined with a suspension of particles of synthetic resin or bloodcells which bear antibodies against one of the enzyme-inhibitor-complexes in question on the surface, and then ascertaining directly whether or not agglutination occurs (agglutination-test).

In connection herewith, it is observed that in methods of immunochemical determination, tests with agglutination-inhibition or direct agglutination are rather generally being used. In the present case, however, a purified enzyme-inhibitor-complex of the blood-coagulation- or fibrinolytic system is applied as well as an antiserum and antibodies against it, and inasmuch as is known, these starting materials have not been applied before.

Moreover, there is no need of ascertaining the presence of the particular complexes always with agglutination or agglutination-inhibition, but also known methods may be used, such as radial immunodiffusion (Mancine-method), quantitative immuno-electrophoresis (Laurell-method), radioimmunoassay and the like.

Furthermore, the invention provides suitable methods of preparing the reagentia to be used in the diagnosis-test, such as the antisera and the suspensions of specially prepared red bloodcells or particles of synthetic resin. These methods of preparation will be described more in detail hereafter.

For the factor to be determined when carrying out the diagnosis-test, on principle any combination of an enzyme and a corresponding inhibitor of the blood-coagulation or fibrinolytic system may be used. In fact, the presence of such a complex always indicates an activation of one or more steps of the blood-coagulation or fibrinolytic cascade and, in consequence thereof, an increased possibility of thrombosis or hyperfibrinolysis. In practice, however, it is a condition that the complexes are rather stable (that they have a relatively long half life time) and may be isolated from bloodplasma in a suitable way, in advance.

Up to now, the following enzyme-inhibitor-complexes have been found to be particularly useful: plasma-antiplasmin-complex, plasmin-$\alpha_2$-macroglobulin-complex and thrombin-antithrombin III-complex. In this connection, it is observed that thrombin and plasmin are known enzymes of the blood-coagulation resp. the fibrinolytic system, whilst antithrombin III is a known inhibitor of thrombin. The material antiplasmin is a recently detected inhibitor of plasmin, and $\alpha_2$-macroglobulin is a material which has been found to be an inhibitor of thrombin as well as inhibitor of plasmin.

The said enzyme-inhibitor-complexes such as they are formed in bloodplasma have not been obtained before in separated state and had not been isolated from activated bloodplasma prior to the invention.

For isolating plasmin-inhibitor-complexes, human blood-plasma activated with streptokinase or urokinase (known enzymes) may be employed. In this way, the plasminogen in the plasma is modified into the plasmin enzyme. The plasmin formed is neutralized in situ rather rapidly by the inhibitors present, namely antiplasmin and $\alpha_2$-macroglobulin. Since plasminogen occurs in two main forms $A_1$ and $A_2$ which also continue in the plasmin formed, at least four enzyme-inhibitor-complexes may be isolated from the activated plasma by column-chromatography, namely plasmin $A_1$-$\alpha_2$-macroglobulin, plasmin $A_2$-$\alpha_2$-macroglobulin, plasmin $A_1$-antiplasmin and plasmin $A_2$-antiplasmin. The isolated fractions may be concentrated and further purified and then combined so that, on the one hand, purified plasmin-$\alpha_2$-macroglobulin and, on the other hand, plasmin-antiplasmin are obtained.

For isolating the thrombin-antithrombin III-complex, one may start from human bloodplasma which has first been defibrinated with the aid of the enzyme reptilase. The defibrinated plasma may be activated by the addition of calcium ions and phospholipides, due to which the coagulation cascade is activated and the available prothrombin is modified into thrombin which is then neutralized by the available inhibitors, namely $\alpha_2$-macroglobulin and antithrombin III. The particular complex of thrombin and antithrombin III may be isolated by chromatography. After concentration and purification it is ready for further use.

From each of the enzyme-inhibitor-complexes an antiserum may be prepared in the customary manner, for instance by injecting rabbits with the complex concerned. After some time, blood is taken from the rabbits and the antisera are collected. The titre of each antiserum may be determined by an agglutination test.

It has been found that the fresh antisera obtained comprise not only specific antibodies against the enzyme-inhibitor-complexes in question but, of course, also various non-specific antibodies. Namely, by immunodiffusion on agargel, the antisera give precipitinlines with respect to fresh bloodplasma. These non-specific antibodies may be made inactive by the addition of fresh bloodplasma so that precipitinlines arise no more. An addition of plasminogenfree plasma is even better. By preference, however, purification is applied so that the titre of the antiserum will not decrease during storage. This purification may be obtained by submitting the fresh antiserum to chromatography over a column of insolubilized bloodplasma obtained, for instance, by coupling fresh or plasminogenfree bloodplasma to agarose activated with cyanic bromide. The specific antibodies then remain in the starting filtrate after which this filtrate is suitable for application as an antiserum in the diagnosis-test.

Another method of purification is that the fresh antiserum is incubated with plasminogen and fresh bloodplasma and then the gamma-globulin-fraction of the antiserum is precipitated and isolated from the mixture. This gamma-globulin-fraction still comprises all of the specific antibodies and is, therefore, suitable for application as an antiserum in the diagnosis-test after resuspension.

Each of the enzyme-inhibitor-complexes may further be used for combination with red bloodcells or particles of synthetic resin for preparing a special reagent for the diagnosis-test. If, for instance, red bloodcells are started from, these may first be tanned in aqueous suspension and then contacted with a buffered solution of one of the enzyme-inhibitor-complexes so as to deposit the complex in question on the surface of the bloodcells. The reagent obtained, provided it is kept in a cool place, retains its keeping quality for a long time and may be used for carrying out a hemagglutination-inhibition-test. Furthermore, an aqueous suspension (latex) of particles of synthetic resin, such as polystyrene or polymethacrylate, may be started from and this may be combined with an aqueous solution of one of the complexes mentioned in a similar way. Similar latices are known for the purpose in view and are commercially obtainable as such.

Another special reagent for the diagnosis-test may be obtained by combining a latex of the particles of synthetic resin just mentioned with an antiserum obtained and purified in the above mentioned manner. The reagent thus obtained, in which the specific antibodies of the antiserum are present on the surface of the particles of synthetic resin, may be used for performing a direct agglutination-test. Likewise, also a suspension of red bloodcells might be started from and these blood cells might be coated with antibodies in a similar manner.

When carrying out the diagnosis-test, an agglutination-inhibiting-test or a test with direct agglutination may be applied. In case of the agglutination-inhibiting-test two reagentia are needed, namely a suspension of red bloodcells or of particles of synthetic resin carrying a purified enzyme-inhibitor-complex on the surface, or an antiserum against the enzyme-inhibitor-complex concerned. The test is then based on an inhibition of the reaction between the two reagentia by enzyme-inhibitor-complex present in the sample of blood to be tested. If the sample of blood comprises the complex in question, a reaction between the complex concerned and the antibodies of the antiserum takes place, so that these antibodies are not available for reaction with the complex on the bloodcells or particles of synthetic resin. If, to the contrary, no enzyme-inhibitor-complex of the type in question is available in the blood sample to be tested, the complex will be able to react freely with the antibodies of the antiserum which finds expression in agglutination of the cells or particles. In practice, various dilutions of the blood sample to be tested are made and it is ascertained at which dilution agglutination exactly takes place. The number thus found is called the titre. High values of the titre (very strong dilution) indicate the presence of enzyme-inhibitor-complexes in the blood sample and, therefore, activation of the blood-coagulation and/or fibrinolytic system.

For the test with direct agglutination, only one reagent is needed, namely a suspension having particles of synthetic resin coated with antibodies against one of the enzyme-inhibitor-complexes in question. The test is based then on a direct reaction between the antibodies on the reagent and an enzyme-inhibitor-complex present in the blood sample to be tested. If the blood sample comprises the complex in question, a reaction takes place which finds expression in agglutination of the particles of synthetic resin. If, to the contrary, the complex in question is not present in the blood sample, agglutination does not take place. A specific titre is obtained by making dilutions of the blood sample and then ascertaining at which dilution agglutination no longer occurs.

The test with agglutination-inhibition takes about 30 to 60 minutes, whilst that with direct agglutination takes about 3 minutes. In case of direct agglutination, however, a false positive reaction (and a high titre), is obtained with persons who have a rheumatism factor in the blood so that an additional determination of the rheumatism factor is necessary.

EXAMPLE I

Isolation of plasmin-inhibitor complexes from bloodplasma

The plasmin-inhibitor-complexes were isolated from bloodplasma activated with streptokinase or urokinase to which traces of radioactive marked plasminogen were added. Isolation was carried out by affinity-chromatography on lysin-agarose and gelfiltration on Sephadex G-200.

Starting materials. Bloodbank plasma of normal donors caught on ACD-coagulant served as starting material. Streptokinase (Kabikinase, of Kabi AB, Stockholm) and urokinase (of Abbott, North Chicago, Ill., U.S.A.) were used as activators. The radioactive marked plasminogen was prepared as follows: human plasminogen was obtained from fresh frozen plasma by affinity-chromatography on lysin-agarose, gelfiltration on Sephadex G-150 and chromatography on DEAE-Sephadex, as described in the thesis of D. Collen, "Plasminogen and prothrombin metabolism in man", University of Leuven, Belgium, 1974. From this strongly purified material, the two main forms of plasminogen were separated by affinity-chromatography on lysin-agarose. The two forms, identified as plasminogen $A_1$ (first peak) and plasminogen $A_2$ (second peak) were marked respectively with $^{125}I$ and $^{131}I$ according to McFarlane, Nature, (London) 182, 53, 1958.

Isolation. Traces of $^{125}I$-plasminogen-$A_1$ and $^{131}I$-plasminogen-$A_2$ were added to portions of 1 liter of bloodplasma, after which the plasma was activated by adding 250 respectively 500 CTA-units of activator per ml of bloodplasma and incubated at room temperature for 30 minutes. Then the activated plasma was conducted through a column of lysin-agarose of 2.5 × 45 cm which was equilibrated with 0.1 M phosphate buffer of pH 7.5, at a speed of 50–70 ml per hour. Non-absorbed protein was removed by washing with equilibration buffer. In these circumstances at least 90% of the radioactivity was retained by the column. Elution was carried out with a linear gradient comprising 500 ml of 0.1 M phosphate of pH 7.5 as starting buffer and 500 ml of 0.1 M phosphate, 0.013 M epsilon-aminocapronic acid with pH 7.5 as final buffer. The elution profile of the radioactivity comprised 6 peaks which, in the sequence of elution, were identified as follows: (1) $^{125}I$-plasmin $A_1$-$\alpha_2$-macroglobulin, (2) $^{131}I$-plasmin $A_2$-$\alpha_2$-macroglobulin, (3) $^{125}I$-plasmin $A_1$-antiplasmin, (4) and (5) $^{131}I$-plasmin $A_2$-antiplasmin and remaining $^{125}I$-plasminogen $A_1$, and (6) remaining $^{131}I$-plasminogen $A_2$.

Various fractions of the chromatogram were concentrated by ultrafiltration and further purified by gelfiltration on Sephadex G-200, the sequence of elution being: $^{125}I$-plasmin $A_1$-$\alpha_2$-macroglobulin complex and $^{131}I$-plasmin $A_2$-$\alpha_2$-macroglobulin complex in the empty volume of the column, (2) $^{125}I$-plasmin $A_1$-antiplasmin and $^{131}I$-plasmin $A_2$-antiplasmin obtained just before the globulin peak by chromatography of plasma and (3) $^{125}I$-plasminogen $A_1$ and $^{131}I$-plasminogen $A_2$ eluted in the valley between globulins and albumens.

The fractions of various Sephadex G-200 columns were combined later on to three large fractions corresponding to the groups 1, 2 and 3 just mentioned. These fractions were dialyzed against distilled water and lyophilized. The average proceeds from eight isolation tests of 1 liter of bloodplasma each were: 14,5 units O.D. at 280 nm per 100 ml of plasma in the first fraction (henceforth indicated as P-$\alpha_2$ M) and 7.3 units per 100 ml of plasma in the second fraction (hereafter indicated as P-AP).

Identification. Under gel-electrophoresis of P-$\alpha_2$ M on SDS-polyacrylamide, a protein band was observed which practically did not migrate into the gel (molecular weight over 400,000). Upon repetition of this test after reduction with dithiothreitol (DTT), various bands were observed of which the principal one had a molecular weight of about 95,000. Immunoelectrophoresis according to Laurell in a gel with $\alpha_2$-macroglobulin-antiserum confirmed the identity of the P-$\alpha_2$ M complex. The complex did not react with antisera against $\alpha_1$-antitrypsin, $C_1$ inhibitor, antithrombin III and inter-$\alpha$-trypsin-inhibitor.

At gel-electrophoresis of P-AP on polyacrylamide, two protein bands were obtained with a molecular weight of around 120,000 and around 140,000. After reduction with DTT, two protein bands were observed with molecular weights of around 65.000 and around 15,000. At immunoelectrophoresis according to Laurell in gels comprising antisera against $\alpha_1$-antitrypsin, $\alpha_2$-macroglobulin, $C_1$-esterase inhibitor, inter-$\alpha$-trypsin inhibitor, antithrombin III and $\alpha_2$-antichymotrypsin, formation of precipitin was not obtained. On the other hand, with this test a reaction was obtained with antiserum generated against the P-AP complex which was absorbed with purified plasminogen. This indicates that P-AP consists of a complex between plasmin and a plasma-protein with antiplasmin properties not identified before, which hereafter will be named antiplasmin.

EXAMPLE II

Isolation of thrombin-antithrombin III complexes from blood-plasma

The thrombin-antithrombin III complexes were isolated from bloodplasma defibrinated with reptilase and of which the coagulation mechanism was activated in the intrinsic way. Isolation was carried out by affinity-chromatography on heparin-Sepharose and gelfiltration on Sephadex G-200.

Starting materials. Bloodbank plasma from normal donors caught on ACD-anticoagulant served as starting material. For defibrinating, reptilase (Defibrase of Pentapharm, Basle) was used, whilst for the activation of the coagulation system calciumchloride and phospholipide (Thrombofax of Ortho Pharmaceutical Company) was used. Moreover, use was made of radioactive marked prothrombin obtained by marking purified human prothrombin with $^{125}$I in the manner of McFarlane.

Activation. Defibrase in an amount of 1 ml per liter was added to portions of 2 liters of bloodplasma after which the plasma was made coagulate for 4 hours at 37° C. and a night in a cold room. The fibrin formed was gradually removed by rolling on a glass bar. A trace of $^{125}$I-prothrombin was added to the defibrinated plasma, after which the coagulation system was activated by the addition of 28 ml of 1 M CaCl$_2$ and 40 ml of Thrombofax per liter of defibrinated plasma. Activation of the coagulation system was followed on the basis of the gradual reduction of the prothrombin present. After about 1 hour the remaining about of prothrombin was less than 5 %.

Isolation. For the affinity chromatography, use was made of heparin-Sepharose which was washed and equilibrated with 0.1 M of tris-HCl, 0.15 M of NaCl, 0.01 M of citrate buffer of pH 7.5. 150 Ml of this herparin-Sepharose (volume after sedimentation) was mixed with 2000 ml of the bloodplasma defibrinated and activated in the above manner for two hours at room temperature. Then the gel was washed on a Buchner funnel with 3 liters of equilibration buffer and poured into a column. The material absorbed was eluted with a salt gradient comprising 500 ml of 0.01 M tris-HCl, 0.15 M NaCl, 0.01 M citrate, pH=7.5, as a starting buffer and 0.01 M tris-HCl, 1 M NaCl, 0.01 M citrate, pH=7.5 as a final buffer.

Three different fractions were obtained thereby: (1) lipoproteins which eluted especially at the beginning of the gradient and the amounts of which varied from preparation to preparation; (2) a thrombin-antithrombin III-complex revealed by simultaneous elution of $^{125}$I and an antigen related to antithrombin III at a salt concentration of around 0.4 M, and (3) remaining antithrombin III eluted after the peak of the foregoing fraction.

The thrombin-antithrombin III-fractions of various tests were combined and concentrated by ultrafiltration. At this stage the preparation was polluted with lipoproteins, as was evident from its turbidity in solution and from its little mobility in a polyacrylamide-gel. Therefore, the preparation was further purified by gelfiltration on a column of Ultrogel AcA 22 of 2.5×45 cm, equilibrated with a buffer of 0.1 M NaCl, 0.05 M phosphate, 0.02% of azide, pH=7,5. Hereby the lipoproteins eluted near the empty volume of the column. The thrombin-antithrombin-complex (hereafter indicated as T-AT) which after purification showed a tendency to the formation of aggregate, eluted in a broad peak. The free antithrombin III eluted later. The T-AT-fractions of various tests, localized by measuring $^{125}$I and an antigen related to antithrombin III, were combined and concentrated by vacuum dialysis. The average proceeds of four isolation tests, each time starting from 2 liters of bloodplasma, amounted to 25 units O.D. per liter of plasma.

Identification. Upon electrophoresis of T-AT on a SDS-polyacrylamide gel, a sharp protein band with a molecular weight of around 65.000 (free antithrombin III) was obtained as hazy bands with slower migration. After reduction with DTT three sharp bands were identified with molecular weights between 65,000 and 95,000, among which were bands of antithrombin III and of thrombin-antithrombin III.

EXAMPLE III

Preparation of antisera

Preparation. Rabbits were immunized with plasmin-antiplasmin-complex (5 rabbits), with plasmin-$\alpha_2$-macroglobulin-complex (2 rabbits) and with thrombin-antithrombin III-complex (4 rabbits). For this purpose, the complexes were solved in a 0.15 M kitchen-salt solution to a concentration of 2 mg per ml and mixed with 1 ml of complete Freund's adjuvant. Each rabbit was injected with one milliliter of this mixture distributed and injected in the soles of the feet, the subcutaneous tissue in the neck and the thigh muscles. Three times after that, each time at an interval of 1 or 2 weeks, an equal amount of antigen was administered, mixed with incomplete Freund's adjuvant and distributed on the subctaneous and intramuscular way. Commencing one week after the fourth injection, 30–80 ml of blood was taken twice per week by puncture of the ear arteries. Each time, the serum of 3 or 4 consecutive blood takings was combined and further worked up together. The titre of the antisera was determined by a hemagglutination test. In a period of 3 months up to 500 ml of serum per rabbit was obtained.

Determination of the titre. For the performance of the agglutination test, a special reagent was prepared comprising red bloodcells which carried a purified complex of the type P-AP, P-$\alpha_2$M or T-AT on the surface. This reagent was made by tanning human red bloodcells of the 0 group and then contacting them with one of the purified complexes in the manner described by Merskey et al for fibrogen breakdown products (see Proc. Soc. Exp. Biol. Med., 131,871,1969). The amounts used of the complexes were: 1 unit O.D. (at 280 nm) of the P-AP-complex, 2 units OD of the T-AT complex and 5 units OD for the P-$\alpha_2$ M-complex, solved in 100 ml of citrate-phosphate buffer. The reagent was stored at 4° C. and used with a month.

Various dilutions of the antisera were made. Each of the dilutions was contacted with a corresponding reagent, after which, the occurrence or non-occurrence of hemagglutination was ascertained. The highest dilution at which clearly visible hemagglutination still occurred was taken as titre of the antiserum concerned. It was found that the values obtained diverged considerably, dependent on the experimental animals used and the moment of blood-taking.

Determination of other valuation-numbers. For obtaining still other valuation-numbers, various agglutination-inhibiting test were carried out with the antisera obtained, in which the antiserum concerned was contacted with the reagent from red bloodcells described above and with a third material, after which the occurrence or non-occurrence, of agglutination was ascertained. Fresh bloodplasma, bloodserum and urokinase-activated plasma served as third material. The serum was obtained by having blood coagulate for 1 hour at 37° C. and comprised less than 5% of remaining prothrombin. The urokinase-activated plasma was obtained by adding 500 CTA units of urokinase per ml to the fresh plasma and incubating this plasma for 30 minutes at 25° C.

In each test the titre of the third material was determined from the dilution at exactly which hemagglutination occurred. Each titre formed the reverse of the dilution found.

Fresh plasma was found to have a titre of 32-512 for T-AT, a titre of 32-64 for P-AP and a titre of 32-128 for P-$\alpha_2$M. Serum inhibited 2-4 times more than plasma for T-AT, while urokinase-activated plasma inhibited 4-16 times better than fresh plasma for P-AP and inhibited 1-2 times better for P-$\alpha_2$M. On the strength of these tests the following valuation numbers were given: a serum-plasma ratio of 2-4 for T-AT and a UK plasma-to-plasma ratio of 4-16 for P-AP and of 1-2 for P-$\alpha_2$M.

Inactivation of non-specific antibodies. By gradual addition of fresh plasma to the antisera (to an amount of 50% vol/vol), the titre of fresh plasma lowered 2-4 times in the tests for T-AT and P-AP and 1-2 times in the test for P-$\alpha_2$M. The ratio between the titres of serum and fresh plasma for T-AT increased 2-4 times, just like the ratio of UK plasma-to-plasma for P-AP.

EXAMPLE IV

Purification of antiserum

The P-AP antiserum obtained according to example IV was purified by chromatography over a column of insolubilized blood-plasma (fresh or plasminogenfree).

Preparation of insolubilized plasma. 75 ml of agarose (sedimented volume) activated with 10 g of CNBr was mixed with 100 ml of coupling buffer (0.1 M NaHCO$_3$, 0.5 M NaCl, pH=9,0) and 10 ml of fresh or plasminogenfree human plasma. In both cases about sixty percent of the protein was bonded to the agarose. The plasminogenfree plasma was a filtrate obtained by chromatography of fresh plasma over lysin-agarose.

Chromatography. Fractions of the substituted agarose were equilibrated with a buffer solution (0.1 M NaCl, 0.05 M phosphate, pH=7.5, or 0.03 M Na$_2$HPO$_4$, 0.05 M KH$_2$PO$_4$, 0.07 M NaCl, pH=6.4) and poured into chromatographic columns. Then the antiserum was carried over the column at a speed of 10 ml/cm$^2$ per hour. Bonded antibodies were eluted with a 0.1 M glycin-HCl-buffer of pH 2.8. The titres in the filtrate and the elution were determined by an agglutination test with the reagent of red bloodcells described above. The separation of specific and non-specific matters was ascertained on the strength of the ratio between the inhibition titres of urokinase-activated plasma and non-activated plasma.

(a) 50 ml of P-AP-antiserum with a titre of 1/512 and a UK-plasma-plasma-ratio of 8 was chromatographed over a column of human plasma-agarose of 1.25×25 cm at a speed of 20 ml/hour. About 25-50% of the agglutinating antibodies was not retained by the column whilst 25-50% could be eluted after absorption. The UK-plasma-plasma-ratio in the filtrate was 16-32 and in the elution 2-4.

Upon rechromatography of the non-absorbed fraction 10-20% of the agglutinating antibodies was not absorbed and 20% was eluted with glycin-HCl. The UK-plasma-plasma-ratio in the filtrate was 32-64 and in the elution 16.

By this double chromatography the total amount of agglutinating bodies was reduced to about 5%, but the UK-plasma-plasma-ratio increased 4-8 times.

(b) 80 ml of P-AP-antiserum with a titre of 1/512 and a UK-plasma-plasma-ratio of 8 was chromatographed over a column of plasminogenfree human plasma-agarose of 1.25×30 cm at a speed of 25 ml/hour. About 90% of the agglutinating antibodies was found back in the filtrate and about 2-5% was eluted with glycine HCl. The UK-plasma-plasma-ratio in the filtrate was 9-16 and in the elution 1-2.

Upon renewed chromatographing of 30 ml of this filtrate again 90% of the agglutinating antibodies was not retained by the column. The UK-plasma-plasma-ratio in the filtrate did no more increase.

EXAMPLE V

Purification of antiserum

A P-AP antiserum obtained according to example III was purified by incubation with plasminogen and fresh bloodplasma separated from the gamma-globulin-fraction and resuspension thereof.

To the fresh antiserum amounts of 1000 KIU aprotinin (Trasylol, of Bayer, Leverkusen, a protease-inhibitor), 0.1 ml of purified plasminogen and 0.16 ml of fresh human bloodplasma were added per milliliter. After 15 minutes incubation at room temperature the precipitate was removed by separation. The above mentioned fluid was diluted 1:2 in a buffer soluton (0.1 M NaCl, 0.05 M phosphate, pH 7.0), after which the gamma-globulin-fraction was precipitated at 4° C. by the addition of ammonium-sulphate to a degree of saturation of 37.5%. After 30 minutes mixing the precipitate was separated off, solved to the original volume of 0.1 M tris-HCL of pH 8.6, dialyzed against this buffer for 2 hours and clarified by separation.

EXAMPLE VI

Bloodcell-reagent for the diagnosis-test

A special reagent for the performance of the clinical diagnosis-test was prepared by providing bloodcells on the surface with a purified P-AP-complex.

Human red bloodcells of the O-group were tanned and contacted with a purified P-AP-complex obtained according to example I, in the manner described by Merskey at al for fibrinogen-breakdown products. One unit OD (at 280 nm) of the P-AP-complex solved in 100 ml of citrate-phosphate-buffer was used. The reagent obtained was kept at 4° C. and was suitable for carrying out an agglutination-inhibiting test.

EXAMPLE VII

Latex reagent for the diagnosis-test

Another special reagent for the performance of the clinical diagnosis-test was prepared by coating the surface of particles of synthetic resin with specific antibodies against P-AP-complex.

A latex of particles of synthetic resin (Bacto-Latex 0.81 of Difco Laboratories, Detroit, Mich., U.S.A.) was washed twice with a buffer solution (0.02 M glycine, 0.03 M NaC, pH 9.0), after which the particles were separated off (Sorvall RC2, 10.000 rpm, 5 minutes) and resuspended in the same buffer solution (1.6 time the original volume). Per ml of suspension, 0.1 ml of gamma-globulin solution was added, obtained according to example V and mixed at room temperature for 60 minutes. The coated particles of synthetic resin were separated off, washed with a buffer solution (0.02 M glycin, 0.03 M NaCl, pH 9.0) and resuspended in another buffer solution (0.1 M glycin, 0.15 M NaCl, pH 9.0) to which 1% of cow's albumin (Povite, Amsterdam) and 0.1% of sodiumazide were added. The reagent obtained was suitable for the performance of a direct agglutination test.

EXAMPLE VIII

Diagnosis-test with bloodcell reagent

When performing the diagnosis-test with the reagent of example VI, various dilution of a bloodplasma sample to be tested were made, after which each of the dilutions was contacted with the reagent in question and with a purified P-AP-antiserum obtained according to example IV b, and then the occurrence, either or not, of agglutination was ascertained. The highest dilution which exactly gave agglutination provided the titre (reverse value).

EXAMPLE IX

Diagnosis-test with bloodcell reagent

When performing the diagnosis-test with the reagent of example VIII, various dilutions of the bloodplasma sample to be tested in a buffer solution (0.1 M glycin, 0.15 M NaCl, 1% of albumin, pH 9.0) were made. On a black plate 20 microliter of each of the dilutions or of the buffer solution alone (blanc test) was mixed with 20 microliter of the latex reagent in question. The suspension was mixed continually by sloping the plate to and fro and the agglutination was read after 3 minutes (+ or −) and after 5 minutes (+ or −).

EXAMPLE X

Outcome of the diagnosis-test

A. When performing the diagnosis-test according to example IX with various samples, clear results could be obtained.

Fresh plasma agglutinated the particles of synthetic resin in dilutions of 1/5 to ⅛ (so that the titre was 5–8), whilst a purified P-AP-complex (in a concentration of 20 mg per 100 ml) showed a titre of 1024 to 2048. When 500 CTA-units of urokinase per ml were added to fresh plasma, followed up by incubation at room temperature, there arose an agglutinating activity which after 30 minutes had reached a titre of 640. This indicates a clear quantification of the P-AP-complexes in the sample activated in vitro.

Fresh serum of a patient with rheumatism-factor in the serum was also found to cause agglutination and, therefore, a high titre. However, by treatment of the serum with insolubilized human gamma-globulins, this agglutinating activity, contrary to the agglutinating activity generated by urokinnase, could be absorbed.

B. Subsequently the diagnosis-test was carried out with blood samples of patients who had undergone a treatment with streptokinase or with repilase. Such a treatment causes a primary resp. secondary activation of the fibrinolytic system, in vivo.

The streptokinase treatment consisted of an intravenous infusion of 600,000 IU for 30 minutes. Blood samples were taken on calcium oxalate (end concentration 0.25%) prior to and 1, 2, 3 and 24 hours after the beginning of the treatment. The repilase treatment consisted of an intravenous infusion of 2 ml reptilase (Defibrase) for 1 hour. The blood samples were taken on trisodium citrate (end concentration 0.313%) prior to and 3, 6, 9, 15 and 24 hours after the beginning of the treatment. The presence of the P-AP-complex in the samples was determined with the methods of examples VIII and IX.

For the samples of the streptokinase treatment, a strong increase of the P-AP-titre was obtained (with both methods) already at the end of the treatment. This titre came up to that of plasma which had been activated in vitro with urokinase. For the first three hours after the treatment, the titres remained almost unchanged and had still increased after 24 hours.

For the blood samples of the reptilase treatment with both methods, also from the end of the treatment to 24 hours thereafter a strongly increased, be it submaximum titre was ascertained which indicates an increased P-AP-content in the plasma. This, therefore, means a secondary activation of the fibrinolytic system.

The results of the test of the blood samples activated in vivo correspond, therefore, to those for samples activated in vitro.

C. With the aid of the diagnosis-test of example IX, P-AP titres in 243 plasma samples emanating from patients of a hospital were determined.

The plasma samples were diluted 1/10 in a buffer solution (0.1 M glycin, 0.15 M NaCl, 1% of albumin, pH 9.0). The samples which generated agglutination were tested on rheumatism factor (RF Latex test, Behringwerke) and, if negative, titred out further. In total 13 samples were positive on rheumatism factor; 163 samples were negative in a 1/10 dilution, 25 samples were positive in a dilution of 1/40 or more.

Of the latter 25 samples the titre was compared with the results of the hemostase-test. In the instances that a titre of 40–80 was found, the hemostase-test had turned out normal. Titres of 120–240 were found with 7 patients of whom the hemostase test had ascertained intravascal coagulation in one case and slight deviations in 4 cases.

These results indicated good usefulness in clinical tests.

What I claim is:

1. A method for purifying an antiserum which has been generated against an enzyme-inhibitor complex, said complex being part of the activated blood coagulation system or fibrinolytic system in blood plasma, comprising the steps of (a) incubating the antiserum with purified plasminogen and fresh blood plasma to form a precipitate and remaining fluid, (b) precipitating a γ-globulin fraction from said remaining fluid and (c) isolating and resuspending said precipitated γ-globulin fraction to obtain a purified antiserum containing only antibodies specific to said enzyme-inhibitor complex.

2. A method as recited in claim 1 wherein said antiserum has been generated against plasmin-antiplasmin-complex.

3. A method as recited in claim 1 wherein the incubation recited in step (a) is conducted in the presence of a protease inhibitor.

4. An antiserum purified according to the method of claim 1.

5. A method of preparing a special reagent for an immunochemical method of determination comprising the steps of contacting a blood cell suspension or a latex of particles of synthetic resin with an antiserum purified by the method of claim 1; and thereby obtaining a suspension or latex in which the antibodies from the antiserum are present on the surface of the said cells or particles.

6. A special reagent for an immuno chemical method of determination prepared according to the method of claim 5.

7. A method of determining an activation of the blood-coagulation and/or fibrinolytic system in blood plasma by determining the presence of specific enzyme-inhibitor-complexes which form part of the said activated systems, comprising the steps of: contacting the blood plasma to be tested with a purified antiserum, obtained by the method of claim 1, against one of the enzyme-inhibitor complexes; subsequently contacting said blood plasma with a suspension of red blood cells or a latex of particles of synthetic resin, which cells or particles carry the particular enzyme-inhibitor-complex; and then ascertaining whether or not agglutination occurs.

8. A method of determining an activation of the blood-coagulation and/or fibrinolytic system in blood plasma by determining the presence of specific enzyme-inhibitor-complexes which form part of the said activated systems, comprising the steps of: contacting the blood plasma to be tested with a latex of particles of synthetic resin or a suspension of blood cells, which particles or cells carry antibodies against one of the enzyme-inhibitor-complexes in question on their surface, as defined in claim 6; and then ascertaining whether or not agglutination occurs.

* * * * *